United States Patent [19]

Kaufman et al.

[11] 4,396,399
[45] Aug. 2, 1983

[54] DETERGENT AND CORROSION INHIBITOR AND MOTOR FUEL COMPOSITION CONTAINING SAME

[75] Inventors: Benjamin J. Kaufman, Wappingers Falls; Harry Chafetz, Poughkeepsie, both of N.Y.

[73] Assignee: Texaco Inc., White Plains, N.Y.

[21] Appl. No.: 278,816

[22] Filed: Jun. 29, 1981

[51] Int. Cl.$^3$ ............................ C10L 1/18; C10L 1/22
[52] U.S. Cl. .............................................. 44/71; 44/63; 252/392
[58] Field of Search ................. 44/63, 71; 252/51.5 A, 252/56 D, 392, 396; 260/343.6

[56] References Cited

U.S. PATENT DOCUMENTS

| | | | |
|---|---|---|---|
| 3,062,631 | 11/1962 | Thompson | 44/71 |
| 3,248,187 | 4/1966 | Bell, Jr. | 44/63 |
| 4,047,899 | 9/1977 | Powell | 44/63 |
| 4,081,456 | 3/1978 | Herba et al. | 44/63 |
| 4,104,477 | 8/1978 | Lavigne | 560/122 |

*Primary Examiner*—Jacqueline V. Howard
*Attorney, Agent, or Firm*—Carl G. Ries; Robert A. Kulason; James J. O'Loughlin

[57] ABSTRACT

As a detergent and corrosion inhibiting fuel additive, the product resulting from the condensation reaction of a $C_9$ to $C_{30}$ alkenylsuccinic anhydride in the presence of a base to form an intermediate spirodilactone followed by the reaction of the intermediate spirodilactone with diethylenetriamine and a fuel composition containing same.

12 Claims, No Drawings

DETERGENT AND CORROSION INHIBITOR AND MOTOR FUEL COMPOSITION CONTAINING SAME

BACKGROUND OF THE INVENTION

1. Field of the Invention

Gasoline compositions are highly refined products. Despite this, they contain minor amounts of impurities which can promote corrosion during the period that the fuel is transported in bulk or held in storage. Corrosion can also occur in the fuel tank, fuel lines and carburetor of a motor vehicle. As a result, a commercial motor fuel composition must contain a corrosion inhibitor to inhibit or prevent corrosion.

Internal combustion engine design is undergoing changes to meet new standards for engine exhaust gas emissions. One design change involves the feeding of blow-by gases from the crankcase zone of the engine into the intake air supply to the carburetor rather than venting these gases to the atmosphere as in the past. Another change involves recycling part of the exhaust gases to the combustion zone of the engine in order to minimize objectionable emissions. Both the blow-by gases from the crankcase zone and the recycled exhaust gases contains significant amounts of deposit-forming substances which promote the formation of deposits in and around the throttle plate area of the carburetor. These deposits restrict the flow of air through the carburetor at low speeds so that an overrich fuel mixture results. This condition produces rough engine idling or stalling causing an increase in the amount of polluting exhaust gas emissions, which the engine design changes were intended to overcome, and decreasing fuel efficiency.

An acceptable motor fuel requires additives addressed to correcting or inhibiting the noted disabling characteristics of motor fuels. Thus, the discovery of a novel and cost effective motor fuel additive capable of general application which combines good detergency properties with effective corrosion inhibition will provide a material advance in the state of the art.

2. Description of the Prior Art

Copending application Ser. No. 190,687, filed Sept. 25, 1980, now abandoned discloses a motor oil dispersant and a process for making the same. The motor oil dispersant disclosed is prepared by condensing an alkenylsuccinic anhydride having an alkenyl group of at least 64 carbon atoms in the presence of a basic catalyst to form an intermediate spirodilactone and then reacting the intermediate spirodilactone with a polyamine or polyamine alcohol to form the dispersant reaction product.

Walter Reppe et al., Ann. 596,158 (1955), reported the conversion of succinic anhydride to the spirodilactone derived from 4-ketopimelic acid by heating at 190°–200° C. in the presence of sodium benzoate (weak base) catalyst as follows:

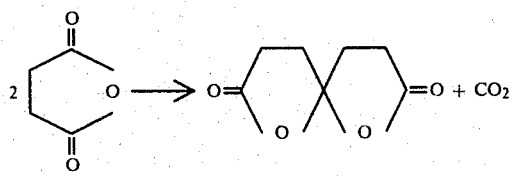

U.S. Pat. No. 4,104,477 is of interest for disclosing spirodilactones prepared by heating alkenyl or alkyl bis (succinic anhydrides) to the temperature at which one mole of $CO_2$ is lost.

SUMMARY OF THE INVENTION

It is the object of this invention to provide a detergent and corrosion inhibiting fuel additive and motor fuel composition containing same.

It has now been discovered that a novel product resulting from the condensation in the presence of a base of an alkenylsuccinic anhydride of the following formula:

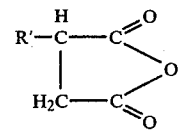

wherein R' is an alkenyl radical having from about 9 to about 30 carbon atoms to form an intermediate spirodilactone, followed by the reaction of the intermediate spirodilactone with diethylenetriamine, is possessed of efficacious detergent and corrosion inhibiting properties when incorporated in a motor fuel composition for an internal combustion engine.

The novel fuel composition of the invention prevents or reduces corrosion during the transportation, storage and the final use of the fuel. The fuel of the invention also is especially effective in its carburetor detergency properties, particularly in its ability to prevent deposit buildup on a clean carburetor.

DESCRIPTION OF THE PREFERRED EMBODIMENTS

The reaction product additive of the present invention is prepared by the condensing in the presence of a base at approximately 250° C. for about 5 hours an alkenylsuccinic anhydride defined by the formula:

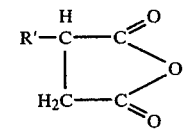

wherein R' is an alkenyl radical having from about 9 to about 30 aliphatic carbon atoms, to form an intermediate spirodilactone, followed by reacting the intermediate spirodilactone with diethylenetriamine at about 100° C. for approximately 2 hours to form the detergent and corrosion inhibiting fuel additive of the invention.

The alkenylsuccinic anhydrides suitable include those of 150 to 450 average molecular weight. These anhydrides can be derived from polyolefins such as polyisobutene, polybutylenes and polypropylene. Preferred alkenylsuccinic anhydrides are those having an average molecular weight of 200 to 350.

A mixture of the prescribed alkenylsuccinic anhydride and the corresponding alkene (containing no more than 1 percent of the alkene) is mixed with the prescribed basic catalyst and heated at an elevated temperature for a sufficient length of time to effect condensation of the alkenylsuccinic anhydride. Usually, the reaction mixture is heated from about 180° to about 270° C., and preferably from 200° to 250° C. for a period of about 5 hours. The carbon dioxide is allowed to escape and any of the non-reactive alkene is removed from the reaction product, leaving a yield of crude spirodilactone.

Suitable base catalysts include inorganic bases such as alkali and alkaline earth carbonates, oxides, hydroxides such as potassium hydroxide, carboxylates, hydrides, and fluorides. Other basic metal salts and stable organic bases such as amines are also operative. Potassium fluoride and potassium carbonate are preferred. The basic catalyst concentration can vary from about 0.1 to about 10 mole % with from about 2 to about 7 mole % being preferred.

Then the crude spirodilactone is admixed with napthenic hydrocarbon oil having an SUS viscosity of 100 at 100° F. The diethylenetriamine is added to the spirodilactone and oil mixture over a period of approximately 0.5 hours. This mixture is then stirred at an elevated temperature ranging from about 80° C. to 140° C. and preferably from about 90° to 110° C., for a sufficient length of time to effect the reaction, usually 2 hours. Finally, the reaction product mixture is filtered to yield the nitrogenous reaction product.

The mole ratio of diethylenetriamine to anhydride condensation product ranges from about 12:1 to about 0.5:1 with the preferred ratio range being from 12:1 to about 2:1, calculated from Sap. No., assuming two saponifiable groups per anhydride molecule.

The polyamine used is diethylenetriamine.

Preparation of the additive of the instant invention is further illustrated but not limited by the following examples:

EXAMPLE I 1000 grams of a tetrapropropenyl-succinic anhydride and tetrapropene mixture (of which no more than 1 percent is tetrapropene) and 0.01 moles (1.7 g) of potassium carbonate were heated at 250° C. for 5 hours. The carbon dioxide was allowed to escape any any tetrapropene removed from the reaction product, leaving 833 grams of crude spirodilactone.

Then, 1.0 moles (113 g) of diethylenetriamine are gradually added over a 30 minute period to 1.0 mole based upon Sap Number 157 (714 grams) of crude spirodilactone in 827 grams of napthenic hydrocarbon oil having an SUS viscosity of 100 at 100° F. This mixture is stirred at 100° C. for 2 hours and filtered to yield 1636 grams of nitrogenous reaction product.

EXAMPLE II 1000 grams of an octadecenylsuccinic anhydride and octadecene mixture (of which no more than 1 percent is octadecene) and 0.01 moles (1.7 g) of potassium carbonate are heated at 250° C. for 5 hours. The carbon dioxide is allowed to escape and any octadecene is removed from the reaction product leaving 840 grams of crude spirodilactone.

Then, 1.0 moles (113 g) of diethylenetriamine are gradually added over a 30 minute period to 1.0 mole based upon a Sap number 136 (826 grams) of crude dispirolactone in 939 grams of napthenic hydrocarbon oil having an SUS viscosity of 100 at 100° F. This mixture is stirred at 100° C. for 2 hours and filtered to yield 1876 grams of nitrogenous reaction product.

In general, the additive is added to the motor fuel composition of the invention in an amount effective to provide carburetor detergency and corrosion inhibition to the fuel composition. The additive is highly effective in an amount ranging from about 0.002 to 0.2 weight percent based on the total fuel composition or 5 to 100 pounds per thousand barrels of fuel (PTB). An amount ranging from about 0.0035 to 0.0188 weight percent is preferred with the most preferred concentration ranging from about 10 to 50 PTB.

The base fuel may consist of straight-chain or branched-chain paraffins, cycloparaffins, olefins, aromatic hydrocarbons, and any mixture of these. The base fuel can be derived from straight-run naphtha, polymer gasoline, natural gasoline or from catalytically reformed stocks, boiling in the range from about 80° to 450° F. and representative of a typical hydrocarbon fuel composition for a spark ignited internal combustion engine. The composition and the octane level of the base fuel are not critical and any conventional minor fuel base can be employed in the practice of this invention.

Alternatively, the base fuel may consist of approximately 90 weight percent of the hydrocarbon mixture described in the immediately preceding paragraph and approximately 10 weight percent ethyl alcohol.

The preferred base fuel in which the additive combination of the invention is employed is a mixture of hydrocarbons boiling in the gasoline boiling range.

The fuel composition of the invention may contain any of the additives normally employed in a motor fuel. For example, the base fuel may be blended with an anti-knock compound, such as a tetramethyl lead, tetrabutyl lead, cyclopentadienyl manganese tricarbonyl, and chemical and physical mixtures thereof, generally in a concentration from about 0.05 to 4.0 cc. per gallon of fuel. The tetraethyl lead mixture commercially available for automotive use contains an ethylene chloride-ethylene bromide mixture as a scavenger for removing lead from the combustion chamber in the form of a volatile lead halide. The motor fuel composition may also be fortified with any of the conventional anti-icing additives, dyes and the like.

Gasoline and gasohol blends were prepared from typical base fuels mixed with specified amounts of the prescribed fuel additive of the invention. These fuels were then tested to determine the effectiveness of the additive fuel. The results obtained in these tests using a commercial detergent gasoline are also given.

Two different base fuels were used to demonstrate the effectiveness of the additive composition of the invention. In the Chevrolet Carburetor Detergency Test, Phase III, gasohol was used as the base fuel, labelled Base Fuel A. Gasohol is composed of 10 weight percent ethyl alcohol and 90 weight percent Base Fuel B (unleaded gasoline).

Base Fuel B, used as the base fuel in the Buick Carburetor Detergency Test and the NACE Corrosion Test is an unleaded grade gasoline having a Research Octane Number of about 93. This gasoline consists of about 32 percent aromatic hydrocarbons, 8 percent olefinic hydrocarbons and 60 percent paraffinic hydrocarbons and boils in the range from 88° to 373° F.

The additive fuel of the invention was tested for its carburetor detergency in the Chevrolet Carburetor Detergency Test. This test is run on a Chevrolet V-8 engine mounted on a test stand using a modified four barrel carburetor. The two secondary barrels of the carburetor are sealed and the feed to each of the primary barrels arranged so that an additive fuel can be run in one barrel and the base fuel run in the other. The primary carburetor barrels were also modified so that they had removable aluminum inserts in the throttle plate area in order that deposits formed on the inserts in this area could be conveniently weighed.

In the procedure designed to determine the effectiveness of an additive fuel to remove preformed deposits in the carburetor, the engine is run for a period of time usually 24 to 48 hours using the base fuel as the feed to both barrels with engine blow-by circulated to an inlet in the carburetor body. The weight of the deposits on both sleeves is determined and recorded. The engine is then cycled for 24 additional hours with a suitable reference fuel being fed to one barrel, additive fuel to the other and blowby to the inlet in the carburetor body. The inserts are then removed from the carburetor and weighed to determine the difference between the performance of the additive and reference fuels in removing the preformed deposits. After the aluminum inserts are cleaned, they are replaced in the carburetor and the process repeated with the fuels reversed in the carburetor to minimize differences in fuel distribution and barrel construction. The deposit weights in the two runs are averaged and the effectiveness of the fuel composition of the invention is compared to the reference fuel which contains an effective detergent additive. The difference in effectiveness is expressed in percent.

TABLE I

CHEVROLET CARBURETOR DETERGENCY TEST PHASE III[a]

| Run/Additive Fuel | Percent Washdown (Removal) of Preformed Deposits |
|---|---|
| 1. Base Fuel A (no carb. deter. added) | −10[c] |
| 2. Base Fuel A + 20 PTB[b] Example I | 63 |
| 3. Premium Fuel Composition C[d] | 62 |
| 4. Premium Fuel Composition D[d] | 66 |

[a]Clean-up type test
[b]PTB is Pounds per Thousand Barrels of Fuel
[c]− denotes a deposit buildup
[d]Runs 3 and 4 were made employing premium commercial detergent fuel compositions.

The foregoing data shows that the motor fuel composition of the invention, illustrated by Run 2, exhibits a surprising improvement over the base fuel, Run 1. The performance of the fuel composition of the invention also is essentially equivalent to that of premium commercial detergent fuel compositions, Runs 3 and 4.

The effect on carburetor detergency of the fuel composition of the invention was also determined in the Buick Carburetor Detergency Test. This test measures the ability of the detergent to prevent deposit build-up on an initially clean carburetor. The test uses a 1973 Buick 350 CID V8 engine equipped with a two-barrel carburetor. The engine was mounted on a dynamometer test stand and had operating and exhaust gas return, an air induction reactor and a positive crankcase ventilator. The test cycle, shown in Table I, is representative of normal road conditions. Approximately 300 gallons of fuel and 3 quarts of oil were required for each run.

Prior to each run, the carburetor was completely reconditioned. Upon completion of the run, the throttle plate deposits were rated visually according to a merit rating scale of 1 to 10 with "1" applied to extremely heavy deposits on the throttle and "10" to a completely clean plate. The test was conducted under various stages. Stage I, Stage II and III, representing different engine operating conditions insofar as engine speed, torque, duration, and the like. Thus, the test was conducted by initially running the engine at 650±25 r.p.m. for one hour followed by three hours at 1500±25 at 80±2 foot pounds torque followed by one hour at 2000±25 at 108±2 foot pounds torque. The cycles were repeated in such order for a total of 120 hours.

TABLE II

1973 BUICK CARBURETOR DETERGENCY TEST OPERATING CONDITIONS

| | Stage I | Stage II | Stage III |
|---|---|---|---|
| Duration - hours | 1 | 3 | 1 |
| Speed, r.p.m. | 650 ± 25 | 1500 ± 25 | 2000 ± 25 |
| Torque, foot pounds | 0 | 80 ± 2 | 108 ± 2 |
| Water out, °F. | 205 ± 5 | 205 ± 5 | 205 ± 5 |
| Carburetor Air °F. | 140 ± 5 | 140 ± 5 | 140 ± 5 |
| Exhaust Back Pressure, in Hg. | — | 0.7 ± 0.1 | |
| Man. Vac., in Hg. | — | 15.8 | 14.2 |
| Fuel flow, pounds per hour | 0.7 | 7.5 | 12.0 |
| Test duration, 120 hours | | | |

The results of this test are set forth in the following table:

TABLE III

BUICK CARBURETOR DETERGENCY TEST

| Run | Fuel Composition | Additive Concentration | Carburetor Rating (Average) |
|---|---|---|---|
| 1 | Base Fuel B | None | 3.2 |
| 2 | Base Fuel B 15[1] | PTB[2] of Example I | 5.3 |
| 3 | Base Fuel B 30[1] | PTB of Example I | 6.6 |
| 4 | Base Fuel B 40[1] | PTB of Example I | 7.1 |
| 5 | Comparison Fuel C[3] | — | 7.2 |
| 6 | Comparison Fuel D[3] | — | 5.2 |

[1]Concentration based on a 50% by weight oil solution of the additive.
[2]PTB = pounds of additive per 1000 barrels of fuel
[3]Commercial unleaded detergent gasoline.

The foregoing results demonstrate that the novel fuel composition of the invention was surprisingly effective for achieving carburetor throttle plate cleanliness as measured by the CRC Varnish rating scale in the Buick Carburetor Detergency Test.

The rust inhibiting effect of the fuel composition of the present invention was determined in the National Association of Corrosion Engineers (NACE) Test.

In this test a mixture of 300 ml of test fuel and 30 ml distilled water is stirred at a temperature of 37.8° C. (100° F.) with a steel specimen completely immersed therein for a test period of 3½ hours. The percentage of the specimen that has rust is determined visually and noted.

The results of this test are set forth in the following table:

TABLE IV

NACE RUST TEST

| Additive in Unleaded Base Fuel B | % Rust[1] |
|---|---|
| 2.5 PTB[2] of Example I | 10–50, 10–50 |
| 5 PTB of Example I | 1–5, 1–5 |
| 10 PTB of Example I | Tr[3]–1, Tr–1 |
| 20 PTB of Example I | Tr–1, Tr–1 |

[1]less than 5% passes test.
[2]PTB = Pounds of additive per 1000 Barrels of fuel.
[3]Tr = Trace The foregoing results demonstrate that the novel fuel composition of the invention was surprisingly effective where preventing the formation of rust and the corrosion of the metal surfaces with which the fuel was in contact.

We claim:

1. A motor fuel composition comprising a base mixture of hydrocarbons boiling in the gasoline boiling range and an effective amount of a detergent and corrosion inhibiting reaction product which is obtained by condensing in the presence of a basic catalyst at temperatures ranging from about 180° C. to about 270° C. an alkenyl succinic anhydride of the formula:

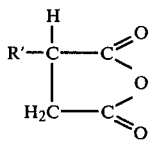

wherein R' is an alkenyl radical having from about 9 to about 30 carbon atoms, to form a spirodilactone intermediate followed by the reaction of the spirodilactone intermediate with diethylenetriamine at from about 80° C. to about 140° C. in which the ratio of diethylenetriamine to spirodilactone intermediate ranges from about 12:1 to about 2:1.

2. A motor fuel composition comprising a base of about 90% of a mixture of hydrocarbons boiling in the gasoline boiling range, about 10% ethyl alcohol, and an effective amount of a detergent and corrosion inhibiting reaction product which is obtained by condensing in the presence of a basic catalyst at temperatures ranging from about 180° to about 270° C. an alkenylsuccinic anhydride of the formula:

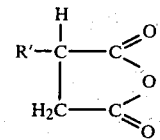

wherein R' is an alkenyl radical having from about 9 to about 30 carbon atoms, to form an intermediate spirodilactone followed by reacting the intermediate spirodilactone with diethylenetriamine at from about 80° C. to about 140° C. where the ratio of spirodilactone to diethylenetriamine ranges from about 12:1 to about 2:1.

3. A motor fuel composition according to claim 1 or 2, wherein said anhydride has an average molecular weight of 100 to 450.

4. A motor fuel composition according to claim 1 or 2 wherein said anhydride has an average molecular weight of 200 to 350.

5. A motor fuel composition according to claim 1 or 2, wherein said basic catalyst is potassium fluoride.

6. A motor fuel composition according to claim 1 or 2, wherein said basic catalyst is potassium carbonate.

7. A motor fuel composition according to claim 1 or 2, wherein said basic catalyst is potassium hydroxide.

8. A motor fuel composition according to claim 1 or 2 containing from 0.0002 to 0.2 weight percent of said detergent and corrosion inhibiting reaction product.

9. A motor fuel composition according to claim 1 or 2 containing from 0.0035 to 0.02 weight percent of said detergent and corrosion inhibiting reaction product.

10. A motor fuel composition according to claim 1 or claim 2 wherein the alkenylsuccinic anhydride is condensed at temperatures ranging from about 200° C. to about 250° C.

11. A motor fuel composition according to claim 1 or claim 2 wherein the spirodilactone intermediate is reacted with diethylenetriamine at from about 90° to about 110° C.

12. A motor fuel composition according to claim 1 or claim 2 wherein the spirodilactone intermediate is reacted with diethylenetriamine at about 100° C.

* * * * *